US012102616B2

United States Patent
Sayed et al.

(10) Patent No.: US 12,102,616 B2
(45) Date of Patent: Oct. 1, 2024

(54) PSILOCIN MUCATE

(71) Applicant: LOBE SCIENCES LTD., Vancouver (CA)

(72) Inventors: Yousry Sayed, Wilmington, NC (US); Frederick Sancilio, Stuart, FL (US); Philip J. Young, Montpelier, VA (US); Shaileshkumar Ramanlal Desai, Wilmington, NC (US); Autumn Beauchamp, Wilmington, NC (US)

(73) Assignee: LOBE SCIENCES LTD., Vancouver (CA)

( * ) Notice: Subject to any disclaimer, the term of this patent is extended or adjusted under 35 U.S.C. 154(b) by 0 days.

(21) Appl. No.: 18/411,576

(22) Filed: Jan. 12, 2024

(65) Prior Publication Data

US 2024/0165080 A1  May 23, 2024

Related U.S. Application Data

(63) Continuation-in-part of application No. PCT/US2023/027500, filed on Jul. 12, 2023.

(60) Provisional application No. 63/388,414, filed on Jul. 12, 2022.

(51) Int. Cl.
  *A61K 31/4045* (2006.01)
  *A61K 9/00* (2006.01)
  *A61P 25/22* (2006.01)

(52) U.S. Cl.
  CPC ........ *A61K 31/4045* (2013.01); *A61K 9/0053* (2013.01); *A61P 25/22* (2018.01)

(58) Field of Classification Search
  CPC .... A61K 31/4045; A61K 9/0053; A61P 25/22
  See application file for complete search history.

(56) References Cited

U.S. PATENT DOCUMENTS

| | | | |
|---|---|---|---|
| 3,078,214 | A | 2/1963 | Hoffmann et al. |
| 11,312,684 | B1 | 4/2022 | Nichols et al. |
| 2004/0242801 | A1 | 12/2004 | Petit et al. |
| 2018/0021326 | A1 | 1/2018 | Stamets |
| 2022/0280482 | A1 | 9/2022 | Barrow et al. |
| 2022/0370413 | A1 | 11/2022 | Barrow et al. |
| 2023/0285359 | A1 | 9/2023 | Barrow et al. |

FOREIGN PATENT DOCUMENTS

| | | | |
|---|---|---|---|
| WO | 2020/157569 | 8/2020 | |
| WO | WO-2020157569 A1 * | 8/2020 | ............ A61K 31/05 |
| WO | 2022/016289 | 1/2022 | |
| WO | 2022/195489 | 9/2022 | |
| WO | 2023/086962 | 5/2023 | |

OTHER PUBLICATIONS

Brown et al. "Pharmacokinetics of Escalating Doses of Oral Psilocybin in Healthy Adults" Clin Pharmacokinet 2017 56:1543-1554.
Clinicaltrialsarena with the extensioncom/news/beckley-psytech-trial-psychedelic-compound/?cf-view Nov. 9, 2022 accessed Jan. 10, 2024.
Finance with the extension yahoo. com/news/tryp-therapeutics-announces-significant-milestone-120000792.html Jan. 8, 2024 accessed Jan. 10, 2024.
Griffith et al. "Psilocybin occasioned mystical-type experiences: immediate and persisting dose-related effects" Pharmaceutica Acta Helvetiae 2011 72 (3) 175-184.
Hasler et al. "Determination of psilocin and 4-hydroxyindole-3-acetic acid in plasma by HPLC-ECD and pharmacokinetic profiles of oral and intravenous psilocybin in man" Pharmaceutica Acta Helvetiae 1997 72(3), 175-184.
Holze et al. "Pharmacokinetics and Pharmacodynamics of Oral Psilocybin Administration in Healthy Participants" Clinical Pharmacology & Therapeutics 2023 113 (4) : 822-831.
International Search Report and Written Opinion in PCT/US2023/027500 dated Oct. 13, 2023.
Kolaczynska et al. "Development and validation of an LC-MS/MS method for the bioanalysis of psilocybin's main metabolites, psilocin and 4-hydroxyindole-3-acetic acid, in human plasma" Journal of Chromatography 2021 B1164 122486.
Lindenblatt et al. "Quantitation of psilocin in human plasma by high-performance liquid chromatography and electrochemical detection: comparison of liquid-liquid extraction with automated on-line solid-phase extraction" Journal of Chromatography 1998 709: 255-263.
Psilocybin Investigator Brochure by Usona Institute Jun. 17, 2021.
Psych with the extension .global/iv-formulation-of-psilocin/ Mar. 22, 2023 accessed Jan. 10, 2024.
Troxler et al. "Abwandlungsprodukte von Psilocybin and Psilocin" Helvetica Chimica Acta 1959 42 (6) : 2073-2103.
Tylš et al. "Psilocybin—Summary of knowledge and new perspectives" European Neuropsychopharmacology 2014 24 (3) : 342-356).

* cited by examiner

*Primary Examiner* — San Ming R Hui
(74) *Attorney, Agent, or Firm* — Licata & Tyrrell P.C.

(57) ABSTRACT

Psilocin formulations of psilocin mucate with improved stability, physical properties and/or handling characteristics, as well as enhanced pharmacologic activity, pharmacokinetic parameters and safety characteristics as compared to psilocin or psilocybin and methods for their use are provided.

20 Claims, No Drawings

PSILOCIN MUCATE

This patent application is a continuation-in-part application of PCT/US2023/027500 filed Jul. 12, 2023 which claims the benefit of priority from U.S. Provisional Application Ser. No. 63/388,414 filed Jul. 12, 2022, teachings of each of which are incorporated herein by reference in their entirety.

FIELD

Psilocin salts, esters and conjugates with improved stability, physical properties and/or handling characteristics, as well as enhanced pharmacologic activity, pharmacokinetic parameters and safety characteristics as compared to psilocin or psilocybin, pharmaceutical compositions containing these psilocin salts, esters and conjugates, and methods for their use in conditions treatable with psilocin are disclosed.

BACKGROUND

Psilocybin, structure of which is depicted in Formula I

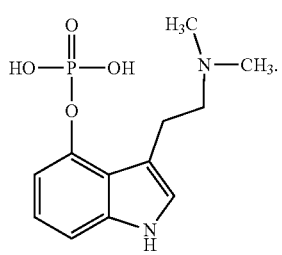

is a phosphate ester prodrug for psilocin as depicted in Formula II

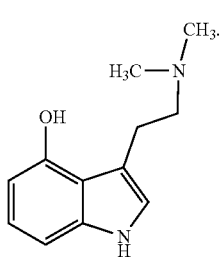

Psilocybin, when taken orally, must undergo a metabolic reaction whereby enzymes convert the inactive prodrug into the active moiety called psilocin. More specifically, psilocybin undergoes an acid catalyzed and/or enzymatic dephosphorylation reaction resulting in a loss of the phosphate group revealing psilocin's hydroxy group. Psilocybin exists as a zwitterion in which the phosphate and amine moiety ionize each other. The existence of a zwitterion limits the solubility of psilocybin and also curtails its ability to make a salt with an alternate acid that could exist under physiologically tolerated conditions. Removing the phosphate group allows the formation of an intermolecular salt of psilocin that is otherwise not possible to be prepared with psilocybin. As a non-ionized form, psilocin is much more lipid soluble in comparison to psilocybin, and therefore is capable of crossing the blood brain barrier more effectively to elicit a response. Psilocin has a high affinity for and is able to activate the 5-HT2A receptor, which plays a key role in regulating mood, sexual behavior, aggression, impulsivity, cognitive function, appetite, pain, sleep, and memory along with other behaviors.

Evidence of therapeutic effects of psilocin in a wide array of clinical applications, including psychiatric conditions, pain disorders, and neurological conditions, has resulted in significant interest in this compound. However, poor physical properties of psilocin in the solid state, e.g. poor crystallinity with limited enhancement of bulk purity upon crystallization, susceptibility to auto-catalyzed oxidation upon handling and prolonged storage, and low water solubility have hampered development of psilocin-based pharmaceuticals.

Classic psychedelics, which are serotonergic hallucinogens, like psilocin, have been shown in multiple lines of research to potentially induce therapeutic changes in people with a variety of psychiatric conditions. However, natural psilocin is only found in relatively smaller amounts in the actual mushroom (Tylš et al. European Neuropsychopharmacology 2014 24(3): 342-356) and unmodified psilocin is relatively unstable in solution. To date, stable forms of psilocin have eluded researchers, and most research has focused on the prodrug, psilocybin, which is metabolized to psilocin after ingestion and responsible for the shown therapeutic and behavioral effects.

Results of completed and published studies have shown psilocin exposure (through psilocybin administration) to results in significant improvement in symptoms of anxiety, depression, and substance use disorder.

Further, psilocin's clinical safety have been extensively studied, both as a single agent and as an adjunctive treatment in adult populations. Psilocin was most commonly administered as psilocybin capsules through oral administration and has been assessed in open-label and double-blind, controlled trials. Dosing regimens for psilocybin have ranged from 0.014 mg/kg to 0.6 mg/kg (which roughly correspond to dose ranges of 7 µg/kg-0.32 mg/kg of psilocin based on estimated dose-normalized bioavailability of 52.7% reported by Hasler et al. (Pharmaceutica Acta Helvetiae 1997 72(3), 175-184)), when administered either as a single dose or multiple escalating doses weeks apart.

Among adverse psychological experiences, the ones often reported following psilocybin administration include anxiety, the induction of negative emotional states, and paranoid or delusional thinking. In relation to physical adverse events, they are cardiovascular (i.e., increased blood pressure and heart rate), as well as nausea and headache. Further, reports of a hallucinogenic effects coupled with increased anxiety have been reports at does as low as 5 mg psilocybin which is equivalent to about 2 mg psilocin. See, e.g. Griffith et al. Pharmaceutica Acta Helvetiae 2011 72(3) 175-184.

The prodrug's pharmacokinetic characteristics have been investigated and reported by several groups including Hasler et al. supra, Lindenblatt et al. (Journal of Chromatography 1998 709:255-263), Holze et al. (Clinical Pharmacology & Therapeutics 2023 113(4):822-831), Kolaczynska et al. (Journal of Chromatography 2021 B1164 122486) and Brown et al. (Clin. Pharmakokinet 2017 56:1543-1554). Data reported in these publications indicate that psilocybin is rapidly converted to psilocin, but its bioavailability seems to vary from paper to paper but is generally reported as about 50-80%. The variation may be attributed to the rate and extent of enzymatic conversion and uptake of the resulting metabolite, psilocin. A drug with a wide range of bioavailability presents problems for formulators and clinical investigation since the variation causes unpredictable results in vivo and in vitro.

Several factors can influence the rate of absorption and conversion of a prodrug such as psilocybin to its active form.

For example, the activity of the enzymes responsible for converting the prodrug into its active metabolite can vary both within an individual and among different individuals. Factors such as genetics, age, and concomitant medication use can influence enzyme activity. Drug-drug interactions can either inhibit or induce enzyme activity, leading to changes in absorption and metabolism rates. Therefore, the rate of conversion may change over time. Another cause for the variability seen is the potential food effect that the prodrug may have. Specifically, work done by Hasler and others under fasted conditions show a markedly lower bioavailability then similar work done by Brown where subjects of the study were fed immediately before the dose was administered.

Further, the prodrug itself may have properties that affect its absorption and conversion. For example, the prodrug's chemical structure, solubility, and stability can impact its absorption rate and how quickly it is converted into the active form.

The formulation of the drug product and the route of administration can also influence the rate of absorption. Different formulations (e.g., immediate-release vs. extended-release) can result in varying absorption profiles, affecting the timing of conversion.

Physiological factors such as gastric emptying time, gastrointestinal motility, and pH in the digestive tract can also affect the rate at which a prodrug is absorbed and subsequently converted into the active metabolite.

In addition, the presence or absence of food in the stomach can impact the rate of absorption and metabolism of a prodrug. In some cases, food may slow down absorption and conversion, while in others, it may enhance them.

In a bioavailability study involving human participants, there can be inter-individual variability in all of the above factors, leading to differences in the rate of absorption and conversion among study participants.

Due to these various factors, it is common for the rate of absorption of a prodrug and its conversion to the active metabolite to exhibit variability over the absorption period in a bioavailability study. Researchers must carefully consider these factors when designing and interpreting such studies to understand the pharmacokinetics and therapeutic implications of prodrugs.

Psilocin itself would be the optimal active substance to use in place of psilocybin, but few have been able to investigate psilocin as the active moiety due to instability.

U.S. Pat. No. 11,312,684 discloses psilocin benzoate and psilocin succinate salts to be preferred salt forms for producing a pharmaceutical composition with superior shelf-life stability, and resistance to oxidative degradation. Stability for up to three weeks is disclosed for some of their salts. Recent disclosures are indicative of testing of these salts as intravenous formulations. See e.g. finance with the extension yahoo.com/news/tryp-therapeutics-announces-significant-milestone-120000792.html, clinicaltrialsarena with the extension com/news/beckley-psytech-trial-psychedelic-compound/?cf-view; and psych with the extension-.global/iv-formulation-of-psilocin/.

An intravenous formulation, with limited stability, is not a practical dosage for commercial use.

There exists a need for psilocin salts, esters and conjugates and formulations thereof with improved stability, physical properties and/or handling characteristics with less patient to patient variability as compared to psilocybin and psilocin which produce the desired anti-anxiolytic pharmacologic effect with limited or no hallucinogenic effect or other serious adverse side effects.

SUMMARY

An aspect of this disclosure relates to the preparation of psilocin salts, esters and conjugates.

Another aspect of this disclosure relates to pharmaceutical compositions comprising these psilocin salts, esters and conjugates.

Another aspect of this disclosure relates to methods for producing these psilocin salts, esters and conjugates.

Another aspect of this disclosure relates to methods for use of these psilocin salts, esters and conjugates and pharmaceutical compositions thereof in treating conditions and diseases treatable with psilocin or psilocybin.

In one nonlimiting embodiment, the psilocin salt is psilocin mucate demonstrated herein to exhibit unexpected advantageous characteristics of stability of at least 12 months, as well as a higher Cmax as compared to an equal amount of psilocin generated by the metabolism of psilocybin when administered orally which corresponds with a desired effect on neurological disorders including, but not limited to, anxiety, depression, cluster headaches, addiction, migraine headaches, obsessive compulsive disorder and other mental health disorders without any hallucinogenic effect or other serious adverse side effects.

Accordingly, other aspects of this disclosure relate to psilocin mucate formulations and methods for improving stability and/or pharmacologic properties and/or safety and/or decreasing patient to patient variability of psilocin via production and/or administration of these psilocin mucate formulations.

More specifically, another aspect of this disclosure relates to psilocin formulations comprising psilocin mucate exhibiting one or more of the following characteristics of at least 95% up to 100% bioavailability of psilocin, at least twice the bioavailability of an equal amount of psilocin generated by metabolism of psilocybin, no food effect upon oral administration, and/or at least a 2-fold decrease in time to maximum concentration (Tmax) as compared to an equivalent oral formulation of psilocybin.

Another aspect of this disclosure relates to oral psilocin formulations comprising psilocin mucate which upon oral ingestion deliver concentrations of psilocin substantially equal to intravenous doses of equivalent psilocybin to a subject.

Another aspect of this disclosure relates to oral psilocin formulations comprising psilocin mucate which exhibit decreased patient-to-patient variability as compared to psilocybin treatment.

Another aspect of this disclosure relates to methods for increasing maximum blood concentration (Cmax) of psilocin in a subject compared to equivalent psilocybin administration via administration of a psilocin formulation comprising psilocin mucate.

Another aspect of this disclosure relates to methods for increasing bioavailability of psilocin in a subject as compared to an equal amount of psilocin generated by metabolism of psilocybin via administration of a psilocin formulation comprising psilocin mucate.

Another aspect of this disclosure relates to method for more rapidly treating a disease or condition in a subject treatable with psilocin or psilocybin as compared to an equivalent amount of psilocybin treatment via administration of a psilocin formulation comprising psilocin mucate.

Yet another aspect of this disclosure relates to methods for producing a psilocin salt with stability for 12 or more months comprising mixing psilocin with galactaric acid (mucic acid).

Definitions

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

Terms such as "a", "an," and "the" are not intended to refer to only a singular entity but include the general class of which a specific example may be used for illustration.

As used herein, the term "about" refers to a value that is within 10% above or below the value being described.

The term "administration" or "administering" refers to a method of giving a dosage of a compound or pharmaceutical composition to a subject.

As used herein, the phrases "pharmacologically effective amount," "therapeutically effective amount," and the like, when used in reference to psilocin salts, esters and conjugates and pharmaceutical compositions comprising these salts, esters and conjugates as disclosed herein, refer to a quantity sufficient to, when administered to the subject, including a mammal, such as a human, which alleviates one or more symptoms of the disease or condition for which the salt, ester or conjugates or composition thereof is administered. The quantity of a given composition described herein that will correspond to such an amount may vary depending upon various factors, such as the given agent, the pharmaceutical formulation, the route of administration, the type of disease or disorder, the identity of the subject (e.g., age, sex, weight) or host being treated, and the like.

As used herein, the terms "treat," "treating," or "treatment" refer to administration of a compound or pharmaceutical composition for a therapeutic purpose. To "treat a disorder" or use for "therapeutic treatment" refers to administering treatment to a subject already suffering from a disease to ameliorate the disease or one or more symptoms thereof to improve the subject's condition (e.g., by reducing one or more symptoms of inflammation). Compositions of the disclosure can also be used as a primary prevention measure, i.e., to prevent a condition or to reduce the risk of developing a condition. Prevention refers to prophylactic treatment of a subject who may not have fully developed a condition or disorder, but who is susceptible to, or otherwise at risk of, the condition. Thus, in the claims and embodiments, the compositions and methods of the disclosure can be used either for therapeutic or prophylactic purposes.

As used herein, the terms "salt", "salts", "salt forms", "conjugate", "conjugates" and "conjugate forms" are interchangeable and are meant to be inclusive of any compounds formed when mixing psilocin with 1-hydroxy-2-naphthoic acid, 2-hydroxy-3-naphthoic acid, galactaric acid (mucic acid), glutamic acid, mandelic acid, naphthalene-2-sulfonic acid, camphorsulfonic acid, pantothenic acid or isethionic acid. Without not being bound to any particular theory, it is believed that salt, ester and conjugate forms of the compounds disclosed herein exhibit binding characteristics in addition to or alternatively from ionic binding of traditional salts which enhances their stability.

Other features and advantages of the disclosure will be apparent from the following Detailed Description, Examples, and Claims.

DETAILED DESCRIPTION

This disclosure provides salt forms, esters and conjugates forms of psilocin, pharmaceutical compositions comprising these salts, esters and conjugates and methods for their production that are useful in any therapies in which psilocin can be used.

Salts, esters and conjugates of this disclosure have the following general formula A:

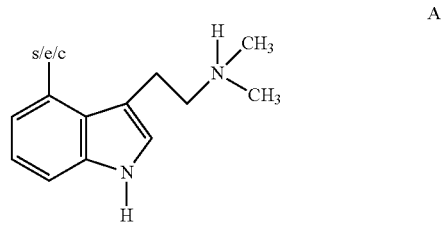

wherein s/e/c of formulation A represents a salt, ester or conjugate.

In one nonlimiting embodiment, the salt, ester or conjugate is prepared from a mixture of psilocin and 1-hydroxy-2-naphthoic acid, 2-hydroxy-3-naphthoic acid, galactaric acid (mucic acid), glutamic acid, mandelic acid, naphthalene-2-sulfonic acid, camphorsulfonic acid, pantothenic acid or isethionic acid, or a reagent such as, but not limited to, chlorosulfonic acid, sulfur trioxide pyridine complex, sulfur trioxide N,N-dimethylformamide complex, sulfur trioxide triethylamine complex or sulfur trioxide trimethylamine complex.

A nonlimiting example of a psilocin salt, ester or conjugate of this disclosure is psilocin isethionate.

Another nonlimiting example of a psilocin salt, ester or conjugate of this disclosure is psilocin mucate.

In one non-limiting embodiment, the prepared salt, ester or conjugate is a zweitter ion. A nonlimiting example of a zweitter ion of this disclosure is psilocin-O-sulfate as depicted in Formula A1

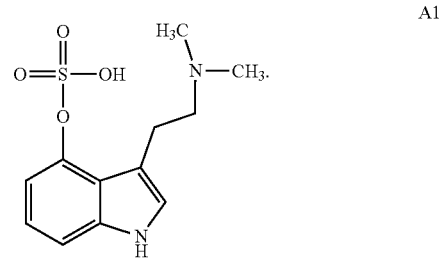 [SMILES: CN(C)CCc1c[nH]c2cccc(OS(=O)(=O)O)c12]

Salts, esters and conjugates of this disclosure exhibit improved stability, physical properties, and/or handling characteristics as compared to psilocin. For example, a psilocin mucic acid conjugate was demonstrated to be stable for at least 12 months. This level of stability for a psilocin salt has never been reported before. Further, studies in human subjects have shown that salts and conjugates of this disclosure exhibit a strong calming effect, also referred to herein as an anti-anxiolytic effect, in patients without the hallucinogenic effect and/or anxiogenic effect often seen with psilocin administration via its prodrug psilocybin at similar doses. Surprisingly, unlike results reported for psilocybin administration such as by Griffith et al. (Pharmaceutica Acta Helvetiae 2011 72(3) 175-184), 9 of 10 subjects administered a psilocin mucic acid conjugate at an equivalent effective dose of 2 mg psilocin had no hallucinogenic effect but a strong suggestion of an anti-anxiolytic effect. These anti-anxiolytic effects at such a low dose, without the hallucinogenic effect were completely unexpected, particularly in a patient population undergoing blood draws often during this same time period. Further, the anti-anxiolytic effect was monitored periodically post-dosing for 28 days and a majority of subjects reported a sustained effect during this period.

Further, not only does psilocin mucate exhibit unexpected advantageous characteristics of stability of at least 12 months, this salt was also determined to have higher Cmax as compared to an equal amount of psilocin generated by the metabolism of psilocybin which corresponded with a desired anti-anxiolytic pharmacologic effect without any hallucinogenic effect or other serious adverse side effects.

Also disclosed herein are pharmaceutical compositions comprising a psilocin salt form, ester or conjugate form of this disclosure and a pharmaceutically acceptable excipient. The pharmaceutical compositions of this disclosure exhibit improved stability, physical properties, and/or handling characteristics as compared to psilocin containing pharmaceutical compositions. Further, studies in patients have shown that salts and conjugates of this disclosure exhibit a strong calming effect in patients without a hallucinogenic effect and/or anxiogenic effect often seen with psilocin administration via its prodrug psilocybin. In particular, psilocin mucate demonstrated unexpected advantageous characteristics of stability of at least 12 months as well as a higher Cmax upon administration as compared to an equal amount of psilocin generated by the metabolism of psilocybin which corresponded with a desired anti-anxiolytic pharmacologic effect without any hallucinogenic effect or other serious adverse side effects. Further, variability resulting from food effect seen in the psilocybin prodrug is not seen for psilocin mucate.

Thus, this disclosure also provides psilocin mucate formulations and methods for improving stability and/or pharmacologic properties including, but not limited to, enhanced bioavailability and/or decreased patient to patient variability of psilocin via production and/or administration of the oral formulation.

In one nonlimiting embodiment, the psilocin formulations comprising psilocin mucate exhibit at least 95%, or up to 100% bioavailability of psilocin.

In one nonlimiting embodiment, the psilocin formulations comprising psilocin mucate exhibit at least twice the bioavailability of an equal amount of psilocin generated by metabolism of psilocybin.

In one nonlimiting embodiment, the psilocin formulations comprising psilocin mucate exhibit no food effect upon oral administration.

In one nonlimiting embodiment, psilocin formulations comprising psilocin mucate exhibit at least a 2-fold decrease in Tmax as compared to an equivalent oral formulation of psilocybin thus providing a more rapid treatment for any disease or condition in a subject treatable with psilocin or psilocybin as compared to an equivalent amount of psilocybin treatment.

In general, dosing regimens found to be useful for psilocybin can also be used for the salts, esters and conjugates of this disclosure. In addition, microdosing, the regular ingestion of a psilocin salt or conjugate as disclosed herein, at very low doses (ranging from 0.5-5 mg, depending on the condition to be treated), may also be a valid dosing approach with therapeutic potential.

In one nonlimiting embodiment, the psilocin mucate is administered orally.

In one nonlimiting embodiment, the psilocin mucate is administered daily.

Examples of a pharmaceutically acceptable excipients include, but are not limited to, biocompatible vehicles, adjuvants, additives, and diluents to achieve a composition usable as a dosage form. Examples of other excipients include colloidal silicon oxide, magnesium stearate, cellulose, sodium lauryl sulfate, and D&C Yellow #10.

Pharmaceutical compositions of this disclosure may comprise one or more solvents, diluents, or other liquid vehicles, dispersions or suspension aids, surface active agents, isotonic agents, thickening or emulsifying agents, preservatives, solid binders, and lubricants, as suited to the particular dosage form desired. Remington's Pharmaceutical Sciences, Eighteenth Edition, E. W. Martin (Mack Publishing Co., Easton, Pa., 1990) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this disclosure. Some examples of materials which can serve as pharmaceutically acceptable excipients include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine; and hydroxypropyl-beta-cyclodextrin and sulfonic acid substituted cyclodextrin (e.g., CAPTISOL™). Commercial grades of lecithin which are preferred include those which are available under the trade name Phosal® or Phospholipon®. and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; 5% dextrose solution and combinations with the foregoing aqueous solutions; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this disclosure can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

When used in the methods and compositions of the disclosure, the pharmaceutically acceptable psilocin salt, ester or conjugate, may be contained in any appropriate amount in any suitable carrier substance formulated for intravenous infusion and is generally present in an amount of 0.01-95% by weight of the total weight of the composition. In particular embodiments, the pharmaceutically acceptable psilocin salt, ester or conjugate is present in an amount of 0.01-5% by weight of the total weight of the composition. In some embodiments, an aqueous solution suitable for intravenous infusion including the pharmaceutically acceptable psilocin salt, ester or conjugate may be formulated in a saline solution. The formulation of infusions is well known to those skilled in the art of pharmaceutical formulation. Formulations can be found in Remington: The Science and Practice of Pharmacy (23rd ed), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). Compositions for infusion use may be provided in unit dosage forms (e.g., in single-dose ampoules), or in vials containing several doses and in which a suitable preservative may be added. The solution of the pharmaceutically acceptable psilocin salt, ester or conjugate suitable for intravenous infusion may have a pH of about 3 and about 9. Furthermore, the solution of the pharmaceutically acceptable psilocin salt, ester or conjugate suitable for intravenous infusion may include a concentration of the pharmaceutically acceptable psilocin salt, ester or conjugate between about 0.1 mg/mL and about 50 mg/mL. In some embodiments, the aqueous solution has between about 1 mg/mL and about 15 mg/mL of any one of pharmaceutically acceptable salts, esters or conjugates of psilocin described herein. In particular embodiments, the aqueous solution has between about 0.1 mg/mL and about 1 mg/mL of any one of pharmaceutically acceptable salts, esters or conjugates of psilocin described herein.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acids, such as, but not limited to, oleic acid and its glyceride derivatives, are useful in the preparation of injectables, as are natural pharmaceutically acceptable oils, such as, but not limited to, olive oil or castor oil, or polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used excipients include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Preferred is that oral formulations such as capsules be packaged in amber glass bottles, secured with polypropylene caps with foam seal liner and maintained until administration at 15-25° C. in a tightly closed container in a dry location.

In one nonlimiting embodiment, the psilocin salt, ester or conjugate is administered in a nasal spray formulation.

In one nonlimiting embodiment, psilocin salt, ester or conjugate is administered by nasal spray transducer programmed time release administration. A nonlimiting device for such administration is described in PCT/US2021/028068 filed Apr. 20, 2021, teachings of which are incorporated herein by reference in their entirety.

In one nonlimiting embodiment, the psilocin salt, ester or conjugate is administered in a nasal spray where a therapeutically active amount of the psilocin salt, ester or conjugate is dissolved or suspended in solution or mixtures of excipients (e.g., preservatives, viscosity modifiers, emulsifiers, buffering agents) in nonpressurized dispensers that deliver a spray containing a metered dose of active ingredient.

Psilocin salts, esters and conjugates of this disclosure and pharmaceutical compositions thereof are useful in methods of treating or alleviating symptoms of any disease or condition treatable with psilocin or psilocybin. Such methods comprise administering a psilocin salt, ester or conjugate of this disclosure to a subject in need in an amount sufficient to treat or alleviate symptoms of the disease or condition. Non-limiting examples of diseases or conditions include a neurological injury, neurodegenerative disease, an inflammatory condition, chronic pain, or a psychological condition. In certain embodiments, the disease or condition is an inflammatory condition (e.g., lung inflammation, neuroinflammation, rheumatoid arthritis, atherosclerosis, psoriasis, type II diabetes, inflammatory bowel disease, Crohn's disease, multiple sclerosis, and/or septicemia). In particular embodiments, the inflammatory condition is chronic obstructive pulmonary disease (COPD), or Alzheimer's disease. In certain embodiments, the disease or condition is a neurological injury (e.g., a stroke, a traumatic brain injury, or a spinal cord injury). In some embodiments, the disease or condition is chronic pain (e.g., pain resulting from postoperative pain, tension headaches, chronic lower back pain, fibromyalgia, nephropathy, multiple sclerosis, shingles, complex regional pain syndrome, cephalic pain, or sciatica). In particular embodiments, the chronic pain condition results from trigeminal autonomic cephalalgia (e.g., episodic and chronic cluster headache (CH), episodic and chronic paroxysmal hemicrania (PH), and short-lasting unilateral neuralgiform headache attacks with conjunctival injection and tearing (SUNCT)). In some embodiments, the trigeminal autonomic cephalalgia is episodic or chronic CH. In certain embodiments, the condition is a psychological condition (e.g., depression, anxiety, addiction, post-traumatic stress disorder, an eating disorder, selective mutism or compulsive behavior). In particular embodiments, the psychological condition is depression or anxiety.

The features and advantages of the psilocin salts, esters and conjugates and compositions prepared therefrom of this disclosure invention are more fully shown by the following examples which are provided for purposes of illustration, and are not to be construed as limiting this disclosure in any way.

EXAMPLES

Preparations of Psilocin Salts, Esters and Conjugates
Materials:
The following acids were used in the preparations of new psilocin salts and conjugates.
1-Hydroxy-2-Napthoic acid
3-Hydroxy-2-naphthoic acid
Galactaric acid (Mucic acid)
L-Glutamic acid
Mandelic acid (R-2-hydroxy-2-phenylacetic acid)
Pantothenic acid
Isethionic acid [2-Hydroxyethylsulfonic acid]
Naphthanlene-2-sulfonic acid
(1S)-(+)-10-Camphorsulfonic acid In addition, a psilocin ester, psilocin-O-sulphate was prepared, which like psilocybin, is a zweitter ion. Psilocin-O-Sulfate can be prepared by reacting psilocin with a number of reagents such as, but not limited to, chlorosulfonic acid, sulfur trioxide pyridine complex, sulfur trioxide N,N-dimethylformamide complex, sulfur trioxide triethylamine complex or sulfur trioxide trimethylamine complex.
General Procedure:
To prepare salts, esters and conjugates, an equimolar or greater quantities of psilocin and the corresponding acid or other reagent were used. Various solvents were used to prepare psilocin salts, esters and conjugates and subsequent recrystallization the salt, esters or conjugate product; the typical solvents used, for example, are methanol, ethanol, Tetrahydrofuran, acetone, ethyl acetate and ether etc.

Example 1

Psilocin, 204.2 mg, (1.0 mmol) and corresponding acid selected from 1-hydroxy-2-naphthoic acid, 2-hydroxy-3-naphthoic acid, galactaric acid (mucic acid), glutamic acid, mandelic acid, naphthalene-2-sulfonic acid, camphorsulfonic acid] (1.0 mmol) were weighed into 8 ml vial and then 2.0 ml Methanol was added while being stirred using a magnetic bar. Precipitates formed right away with mucic acid and 1-hydroxy-2-naphthoic acid. All other salts or conjugates formed clear solutions with the exception of glutamic acid which formed a gooey mass.

The precipitates were collected on a frit after diluting with about 4 mL of ethyl acetate. The collected products were washed successively with ethyl acetate and ether, and then dried under high vacuum.

In reactions where no precipitates were formed, the clear solutions were transferred into a small round bottom flask. The solvents were removed using rotavapor; foam was formed when high vacuum was applied. The foam was then treated with the combination of solvents including, but not limited to, ethyl acetate, acetone, tetrahydrofuran and ether to precipitate the product.

Example 2

A pantothenic acid salt of psilocin was prepared as described below. Calcium pantothenate, 476.6 mg (1.0 mmol) was dissolved in 2.0 ml of deionized water treated with 2.0 ml of 1N HCL; a clear solution was obtained. This solution was added to stirring solution of psilocin, 408.4 mg (2.0 mmol) in 2.0 ml methanol. After stirring at room temperature for 2 hours, solvents were removed and drying at high vacuum yielded a white solid containing the pantothenic acid salt of psilocin and 1 mmol of calcium chloride.

Example 3

An isethionic acid salt of psilocin was prepared as given here. The isethionic acid sodium salt, 145.4 mg (1.0 mmol) was dissolved in 2.0 mL of deionized water and treated with 1.0 ml of 1N HCL; a clear solution was obtained. This solution was added to the stirring solution of psilocin, 204.2 mg (1.0 mmol) in 3.0 ml methanol. After stirring at room temperature for 2 hours, solvents were removed and drying at high vacuum yielded a white solid containing the isethionic acid salt of psilocin and 1 mmol of sodium chloride.

Example 4

Psilocin-O-sulfate was prepared, for example, by treating the solution of psilocin, 204.0 mg (1.0 mmol) in 5.0 mL of Pyridine with sulfur trioxide pyridine complex, 318.3 mg (2.0 mmol). The reaction continued overnight, and then, solvent removed under high vacuum. Cold water was added to the residue and insoluble product collected on frit. The product was washed with cold water and methanol and dried under high vacuum. The recrystallization from methanol yielded pure product.

Example 5: Purity Evaluations

Purity evaluations were performed by high pressure liquid chromatography (HPLC) on the following psilocin salts, esters and conjugates.

| Salt/Ester/Conjugate | Molecular Weight |
|---|---|
| Psilocin Mucate | 414.30 |
| Psilocin OH Naphthalic | 392.30 |
| Psilocin Mandelic | 356.30 |
| Psilocin Pantothenic[1] | 534.38 |
| Psilocin O-Sulfate | 284.2 |
| Psilocin Base | 204.27 |

[1]Contains approximately one mole of •CaCl$_2$

Chromatographic purity, assay, and identification by retention time of the synthesized psilocin salts, esters and conjugates was determined using reverse phase HPLC. Chromatographic separation was performed on a 4.6×250 mm, 5 µm column Zorbax SB-Phenyl using gradient elution and UV detection at 220 nm. The psilocin salts, esters and conjugates were also analyzed for identification from 200 nm to 400 nm using diode array detection. The chromatographic conditions used are shown in Table 1. Stock solutions of the samples were prepared in methanol at approximately 0.5 mg/mL Psilocin. The samples were diluted five-fold in dilute acetic acid (0.2% v/v) to an approximate concentration of 0.1 mg/mL Psilocin in dilute acetic acid:methanol 80:20. The purity value was determined using peak area percent. Assay values for the psilocin salts, esters and conjugates were calculated using psilocin base as an external reference standard. The assay value is on the "as is" basis and does not take into account moisture, residual solvents, or inorganic impurities. The retention time and UV spectrum for the Psilocin O-sulfate did not yield a positive identification for Psilocin. Results are shown in Table 2.

TABLE 1

HPLC Chromatographic Conditions

| Parameter | Experimental |
|---|---|
| Column | 4.6 × 250 mm, 5 μm column Zorbax SB-Phenyl or equivalent |
| Column temperature | 25° C. |
| Mobile phase | MPA - 94.5:0.5 Water:$H_3PO_4$ MPB - Acetonitrile |
| Flow rate | 1.0 mL/minute |
| Injection volume | 10 μL |
| Autosampler temperature | Ambient |
| Detector | 220 nm (200-400 nm for PDA) |
| Run Time | 25 minutes |
| Quantitation | Area percent |
| Approx. Retention Time | Psilocin ~14 minutes |

| Gradient | Time (minutes) | % MPA | % MPB |
|---|---|---|---|
| | 0.0 | 95 | 5 |
| | 12.0 | 85 | 15 |
| | 20.0 | 85 | 15 |
| | 20.5 | 95 | 5 |
| | 20.0 | 95 | 5 |

TABLE 2

Results for Assay, Chromatographic Purity, and Identification

| Lot No. | Chromatographic Purity (% Area) | Assay (as is % w/w) | Retention Time (minutes) |
|---|---|---|---|
| QCL-SD-Mucate | 100.0 | 98.1 | 14.6 |
| QCL-SD-OH naphthalic | 100.0 | 99.2 | 14.7 |
| QCL-SD-mandelic | 100.0 | 98.3 | 14.7 |
| QCL-SD-pantothenic | 99.9 | 82.3[1] | 14.7 |
| QCL-SD-O-sulfate[2] | 98.8 | N/A | 12.6[3] |
| QCL-SD-Psilocin | 100.0 | N/A | 14.7 |

[1]Contains approximately one mole of •$CaCl_2$, corrected assay value is 103.8%
[2]O-sulfate is an ester on the phenolic hydroxyl group
[3]Does not match for psilocin positive identification (UV spectrum and retention time)

Example 6: Stability Studies on Psilocin Mucate

Additional stability studies were performed on psilocin mutate (also known as psilocin mucic acid salt or conjugate or psilocin galactaric acid salt or conjugate) capsule over a 12 month period.

Appearance was evaluated by viewing of the sample on a watchglass over a black and white background.

Assay conditions for Test/Method TM-022-0392 assessing stability and impurities were as follows:

Mobile phase: MPA: 945 mL water, 5 mL $H_3PO_4$, pH to 5.7 with NaOH; MPB: Acetonitrile
Diluent: 80:20 Water:MeOH
Standard: 0.4 mg/mL Psilocin Mucic RS in Diluent
Sample: 0.4 mg/mL Psilocin Mucic API in Diluent
HPLC Conditions are depicted in Table 3.

TABLE 3

| Column | 4.6 mm × 250 mm, 5 μm column Zorbax SB-Phenyl or equivalent |
|---|---|
| Column temperature | 35° C. |
| Mobile phase | MPA - 94.5:0.5 Water:$H_3PO_4$ MPB - Acetonitrile |
| Flow rate | 1.0 mL/minute |
| Injection volume | 10 μL |
| Autosampler temperature | Ambient |
| Detector | 220 nm (200-400 nm for PDA) |
| Run Time | 45 minutes |
| Quantitation | Area percent |
| Approx. Retention Time | Psilocin ~15 minutes |

| Gradient | Time (minutes) | % MPA | % MPB |
|---|---|---|---|
| | 0.0 | 95 | 5 |
| | 16 | 85 | 15 |
| | 20 | 85 | 15 |
| | 40 | 75 | 25 |
| | 40.1 | 95 | 5 |
| | 45* | 95 | 5 |

*Additional equilibration may be required

System suit: RSD NMT 2.0% (5 injections), Tailing NMT 2.0, Plate count NLT 10000

Calculations were against a bracketing external standard.

Identity of psilocin mucate was verified by ultraviolet (UV) assessment, wherein the UV spectrum of the main peak in the standard matched the UV spectrum of the main peak in the sample and by retention time wherein the retention time ratio was 0.98-1.02.

Results are depicted in Table 4.

TABLE 4

| Test/Method | Specification | Initial | 1 Month | 3 Months | 5 Months | 6 Months | 12 Months |
|---|---|---|---|---|---|---|---|
| Appearance POL-0018 | Product: White to light brown powder partially filling white opaque capsules | Conforms | Conforms | Conforms | Conforms | Conforms | Conforms |
| | Packaging: Labeled, amber glass bottle with white closure containing 15 partially filled white opaque capsules | Conforms | Conforms | Conforms | Conforms | Conforms | Conforms |

TABLE 4-continued

| Test/Method | Specification | Initial | 1 Month | 3 Months | 5 Months | 6 Months | 12 Months |
|---|---|---|---|---|---|---|---|
| Assay TM-22-0392 | 90.0-110.0% (% Label Claim) | 98.8% | 98.8% | 101.1% | 103.2% | 98.8% | 98.4% |
| Impurities TM-22-0392 | Report all impurities 2'.0.05% | RRT 1.12/0.08% | RRT 1.11/0.05% | All < 0.05% | All < 0.05% | All < 0.05% | All < 0.05% |
|  | Total Impurities- Report Results | 0.08% | 0.05% | <0.05% | <0.05% | <0.05% | <0.05% |

| | | Prep | % w/w | Prep | % w/w | Prep | % w/w | Prep | % w/w | Prep | % w/w | Prep | % w/w |
|---|---|---|---|---|---|---|---|---|---|---|---|---|---|
| Water Content by cKF TM-22-0012 | NMT 10.0% | 1 | 1.1 | 1 | 0.9 | 1 | 2.0 | 1 | 1.2 | 1 | 1.4 | 1 | 1.2 |
| | | 2 | 1.2 | 2 | 0.8 | 2 | 1.1 | 2 | 1.3 | 2 | 1.4 | 2 | 1.3 |
| | | Mean (2) | 1.2 | Mean (2) | 0.9 | Mean (2) | 1.6 | Mean (2) | 1.3 | Mean (2) | 1.4 | Mean (2) | 1.3 |

Example 7: Phase One, Open-Label, Single-Treatment, Single-Dose, Single-Period, Pharmacokinetic Study of Hard Gelatin Capsules Containing Psilocin as its Mucic Acid Conjugate Form For this study, psilocin mucate, a tryptamine derivative presenting as a white to light brown solid, crystalline powder was administered. The molecular weight of this compound 414.41 g/mol. With respect to equivalency, 4.05 mg of psilocin mucate is equivalent to 2 mg of psilocin. In humans, the mucic acid is enzymatically cleaved in the body during metabolism to produce psilocin, which serves as an agonist to various serotonin receptors including the 5-HT2A receptor, which underlies psilocin's hallucinogenic and therapeutic effects (Cao et al. Science (New York, N.Y.) 2022 375(6579):403-411; Lowe et al. Molecules 2021 26(10), 2948). For this clinical study psilocin was provided as white/opaque hard gelatin capsules containing 4.05 mg of the psilocin mucic acid conjugate equivalent to 2 mg psilocin. A single capsule was administered orally, with water to 10 healthy subjects ages between 21 and 50 years, body-mass index 18.5 to 30.0 kg/m 2 inclusive (minimum of 50 kg weight for males and 45 kg for females), non-smokers or quit smoking 24 hours prior to dosing. The aim of the study was to assess the bioavailability and pharmacokinetic parameters, including the rate and extent of absorption of psilocin mucate, by measurement of plasma concentrations of psilocin and calculations from those measurements and to show any serious adverse events and potential medicinal properties of this psilocin salt.

Blood collection (8 mL) was performed in K3 EDTA blood tubes under sodium light at pre-dosing (−1.00) and at 0.25, 0.50, 0.75, 1.00, 1.50, 2.00, 3.00, 5.00, 8.00, 12.00, 16.00 and 24.00 hours after dosing.

The total number of blood collections in study period was 13.

In addition, a psychiatrist independent from the principal investigators of the study assessed the "mood" of each subject and gave each subject the mini mental state examination (MMSE) test to determine if the subject's score was lowered. The MMSE test is an 11-question measure that tests five areas of cognitive function: orientation, registration, attention and calculation, recall, and language. The MMSE scores, when a hallucinogenic substance is dosed, are expected to go down below 25 Results are depicted in the following Table 5.

TABLE 5

| SUBJECT NO. | MMSE | FEELING STATUS |
|---|---|---|
| 01 | 27 | More relaxed, want to drink sweet tea, better mood |
| 02 | 29 | Better mood, feels hyper sexual |
| 03 | 28 | Felt high mood, now he feels in good way, , he would love to take IMP daily |
| 04 | 29 | Less anxious, better mood, increase his appetite |
| 05 | 30 | Feel little beet happier, better energy |
| 06 | 28 | Feel calm, less thoughts, happier mood |
| 07 | 28 | Euphoric, better mood, it helps with life stress |
| 08 | 27 | Euphories, better mood, sleepy, feel time is slower |
| 09 | 30 | Sleepy, better thoughts, less worried in general |
| 10 | 30 | Did not feel change in mood but feeling cold extremities. |

Surprisingly, unlike results reported for psilocybin administration such as by Griffith et al. (Pharmaceutica Acta Helvetiae 2011 72(3) 175-184), 9 of the 10 subjects administered the psilocin mucic acid conjugate had no hallucinogenic effect but a strong suggestion of an anti-anxiolytic effect. These anti-anxiolytic effects at such a low dose, without the hallucinogenic effect was completely unexpected, particularly in a patient population undergoing blood draws often during this same time period. Further, the anti-anxiolytic effect was monitored periodically post-dosing for 28 days and a majority of subjects reported a sustained effect during this period.

Also surprising was that after correcting for the molar differences between psilocybin and psilocin mucate, the data showed that psilocin mucate has a much higher bioavailability (BA) than expected. The Cmax (highest concentration found in the blood after dosing) data indicates that psilocin mucate has at least twice the BA compared with psilocybin reported in all of the published studies. Psilocybin is reported to be 36% BA compared to psilocin mucate by Hasler, 44% by Lindenblatt, approximately 50% by Holze and between 50-60% by Brown. Overall, the BA of psilocin mucate, is superior and about double that of psilocybin as reported.

Further, the shape of the BA curve, that is the concentration versus time curve showed that psilocin following administration of the mucate salt form, is essentially eliminated from circulation in less than 12 hours, with little variation between subjects. This may allow psilocin mucate to be dosed more frequently than psilocybin which has an irregular elimination rate. For example, administration of psilocin via psilocin mucate may allow for daily dosing of the drug, preferably orally, rather than weekly dosing as is customary for psilocybin whose clearance is long and inconsistent.

In addition, the reported anti-anxiolytic effect in subjects corresponded to the Cmax interval.

Further, no serious adverse effects were reported although one subject reported slight and transient dizziness during the study.

Comparative pharmacokinetic parameters of this study with psilocin mucate (PM) versus results from published studies with psilocybin are shown in Table 6.

Surprisingly, this comparison showed a psilocin formulation of psilocin mucate of this disclosure to exhibit at least 95% up to 100% bioavailability of psilocin, at least twice the bioavailability of an equal amount of psilocin generated by metabolism of psilocybin, no food effect upon oral administration and at least a 2-fold decrease in Tmax as compared to an equivalent formulation of psilocybin. The oral psilocin formulation of psilocin mucate delivered concentrations of psilocin equivalent to intravenous doses of psilocybin to these subject and exhibited decreased patient-to-patient variability as compared to psilocybin treatment.

istered to the male and female mice in the vehicle control group (G1 and G1R) for 28 consecutive days. Oral administration was done at a fixed dose volume of 10 mL/kg bw.

The stability of the psilocin mucate formulation was determined before starting the treatment up to 10 days at 2-8° C. Dose formulations were prepared and administered to mice allocated to their respective dose groups within the stability period.

The formulation analysis was performed during first and last formulation preparation. The results revealed that the formulations were considered acceptable as the overall mean concentrations were within 110% (101.46% to 103.33%) of the nominal concentrations, and the relative standard deviations (RSD) were ≤10% (0.04 to 1.69).

Parameters including mortality and morbidity check, clinical signs of toxicity, detailed clinical signs observation, functional observation battery, ophthalmological examinations, weekly body weights, weight changes and weekly feed consumption were evaluated. Blood and urine samples were collected at the end of the treatment and recovery periods for clinical pathology investigations. All the animals were subjected to a detailed gross necropsy and specified organs were conducted and weighed. The histopathological examinations were carried out on the preserved organs of vehicle control (G1) and high dose (G4) main group mice.

TABLE 6

| Actual Study dose | Psilocin Dose | Per Kg Dose | Cmax | Tmax | AUC μG H/L |
|---|---|---|---|---|---|
| 1 mg i.v. PY by Hasler | 0.718 mg | 0.01 mg/kg i.v. | 12.9 ng/ml | 1.9 min | 4 |
| 0.224 mg/kg p.o. PY fasted by Hasler | 0.161 mg/kg | 0.161 mg/kg p.o. | 8.2 ng/ml | 105 min | 32.71 |
| 2 mg p.o. PM fasted | 2 mg | 0.026 mg/kg p.o. | 3.66 ng/ml | 0.75 hr | 11.189 |
| 25 mg p.o. PY fasted by Holze | 17.95 mg | 0.256 mg/kg | 17 ng/ml | 1.9 hr | 83 |

Example 8: Toxicity Study in Swiss Albino Mice

The objective of this study was to determine the potential toxicity of psilocin mucate following oral (gavage) administration to Swiss Albino Mice for 28 consecutive days and to assess the reversal/delayed occurrence of toxicity by a recovery period of 14-days after cessation of the treatment. The study was designed to provide information on major toxicity and target organ toxicity to estimate the No Observed Adverse Effect Level (NOAEL) which will be used for establishing safety criteria for human exposure and a basis for the subsequent long-term studies.

Doses of 0, 2, 10 and 20 mg/kg bw/day of psilocin mucate were selected based on the human dose of 9 mg/day based on available literature such as the Psilocybin Investigator Brochure by Usona Institute. Derived human equivalent dose for mice is approximately 2 mg/Kg bw/day and 1×, 5× and 10× of this dose level was considered for G2, G3 and G4 groups respectively. Milli-Q water was selected as a vehicle for formulation preparation based on the results of a solubility test performed at the test facility.

After acclimatization, 36 males and 36 female mice were assigned randomly to six dose groups (6 animals/sex/group) using body weight based stratified randomization.

Psilocin mucate in Milli-Q water was administered by oral route to animals in both sexes at the doses of 2 (G2), 10 (G3) and 20 (G4 and G4R) mg/kg bw/day for 28 consecutive days. Similarly, the vehicle (i.e. Milli-Q water) was admin- Results were as follows:
Mortality and Morbidity Check
  No mortality or morbidity was observed at any dose level.
  Clinical Signs and Detailed Clinical Signs Observation
  No clinical signs of toxicity were observed during the treatment and recovery period.
Functional Observation Battery
  No treatment related effects were observed during functional observation assessment.
  A statistically significant increase was observed in foot splay measurement measured during the last day of recovery period in G4 recovery group females compared to the respective control group. This change was considered a random biological variation and not due to treatment.
Ophthalmological Examination
  No ocular abnormalities were observed in any of the animals before the start of the treatment or at the last day of treatment for main group animals and last day of observation for recovery group animals.
Body Weights and Body Weights Gains
  In males, a statistically significant decrease in body weight gain was observed in G4 males between day 1-8 compared to respective control group.
  In females a statistically significant increase in the net body weight gain (day 1 to day 43) was observed in G4 recovery females compared to the respective control group.
  The statistically significant decrease observed in body weight gain in males was not considered as an adverse effect of treatment as animals adapted and no such effects were observed in the following weeks.

The statistically significant changes observed in net body weight gain in recovery females was due to individual animal variation and not due to treatment.

Food Consumption

In males, a statistically significant increase in feed consumption was observed during day 29-36 in the G4 recovery group compared to the respective control group. This change in feed consumption was considered as incidental and not due to treatment.

Hematology Parameters

No psilocin mucate related changes were observed in any of the hematological parameters in both sexes.

In males, a statistically significant decrease in relative eosinophil count was observed in G2 and G4 when compared to vehicle control group (G1) and a statistically significant increase in red blood cells and hemoglobin and decrease in reticulocytes was observed in G4R when compared to control group G1R.

In females, a statistically significant increase in white blood cells and platelets was observed in G4 when compared to vehicle control group and an increase in mean corpuscular hemoglobin in G4R was observed when compared with vehicle control group G1R.

In males, changes observed in main group lacked dose dependency. In recovery males, similar changes were not observed in main group and present only in single sex.

In females, changes observed in main group were not correlating with any other related parameters, gross pathology, and histopathology. In recovery females, similar change was not observed in main group and present only in single sex.

Hence, all these changes observed in hematology parameters were considered as not related to psilocin mucate and toxicologically irrelevant.

Coagulation Parameters

No statistically significant changes were observed in any of the coagulation parameters in both sexes in both main and recovery group.

Clinical Chemistry

No psilocin mucate related changes were observed in clinical chemistry parameters in both the sexes.

In males, a statistically significant increase in inorganic phosphorous in G4 compared to vehicle control group and decrease in chloride in G3 compared to G1 was observed.

In females, a statistically significant increase in total bile acids in G3 and G4 group compared to vehicle control group G1, increase in creatinine, total protein, albumin and calcium and a decrease in aspartate aminotransferase and inorganic phosphorous in G4R compared to vehicle control group G1R was observed.

In males, change in chloride was observed only in G3 group and not in G4 group; change in inorganic phosphorous were not correlating with related parameters, gross pathology and histopathology.

In females, change observed in total bile acids was not correlating with any other related parameters, gross pathology and histopathology and the changes observed in recovery females were not observed in main group animals.

Hence, all these changes observed in clinical chemistry parameters were considered as not related to psilocin mucate and toxicologically irrelevant.

Acetyl Cholinesterase (AChE) Estimation

No psilocin mucate related changes were observed in AChE level. A statistically significant increase in AChE was observed in G4 male and G3 female animals in comparison to vehicle control recovery group.

The change observed in male was present only in single sex and in female lacked dose dependency. Hence, these changes were considered as non-psilocin mucate related.

Urinalysis

No psilocin mucate related changes were observed in urinalysis parameters.

A statistically significant decrease in pH was observed in recovery female group (G4R) in comparison to vehicle control recovery group.

These changes were considered as not related to psilocin mucate as similar changes were not observed in main group.

Gross Pathology

No gross changes were observed in any of the group in both the sexes.

Organ Weight

In male animals, a statistically significant decrease in absolute and relative lungs weight and absolute prostate with seminal vesicles and coagulating gland weight was observed in recovery group (G4R) in comparison with vehicle control group (G1R).

In female animals, a statistically significant increase in absolute and relative thymus weight was observed in G4 group in comparison with vehicle control group (G1) and decrease in relative adrenals and brain weight was observed in recovery group (G4R) in comparison with vehicle control group (G1R).

These changes were considered not psilocin mucate related as change observed in main group could not correlate with any change in gross and histopathology. In recovery groups, changes observed were not correlated with main group changes and present only in single sex.

Histopathology

There were no psilocin mucate related histopathological changes in the any of the organs/tissues examined.

A single incidence of cortical cyst (unilateral) in kidneys of G4 female, hepatocellular necrosis (focal and minimal in severity) in liver of G1 male and presence of luteal cyst (unilateral) in ovaries of G4 female were observed. These lesions were observed in control and high dose group animals and are common background findings in mice. Hence, considered as toxicologically irrelevant and not related to psilocin mucate.

CONCLUSION

Repeated administration of psilocin mucate API to Swiss Albino mice for 28 consecutive days had no psilocin mucate related effects on the general health of the animals, mean body weight, body weight changes, feed consumption, clinical pathology parameters, gross pathology and histopathology in both sexes. No psilocin mucate related effects were observed during the 14-day recovery period after cessation of the treatment.

Based on the observed results under the experimental conditions employed in the study, it is concluded that the NOAEL of the psilocin mucate is equal to 20 mg/kg bw/day. This translates to a dose of 1,400 mg for an average person of 70 kg, which is higher than expected.

The lethal dose 50% (LD50) reported in Usona's investigator's brochure for psilocybin is reported to be 285 mg/kg. For psilocin mucate, no mortality or morbidity was observed at any dose level, hence no estimated LD50 can be calculated.

What is claimed is:

1. A psilocin formulation comprising psilocin mucate, said formulation exhibiting:
   at least 95% bioavailability of psilocin; and/or
   at least twice the bioavailability of an equal amount of psilocin generated by metabolism of psilocybin; and/or
   no food effect upon oral administration; and/or
   at least a 2-fold decrease in time to maximum concentration (Tmax) as compared to an equivalent formulation of psilocybin.

2. The psilocin formulation of claim 1 exhibiting:
   at least 95% bioavailability of psilocin;
   at least twice the bioavailability of an equal amount of psilocin generated by metabolism of psilocybin;
   no food effect upon oral administration; and
   at least a 2-fold decrease in Tmax as compared to an equivalent formulation of psilocybin.

3. The psilocin formulation of claim 1 administered orally to a subject.

4. The psilocin formulation of claim 1 administered daily to a subject.

5. An oral psilocin formulation comprising psilocin mucate which upon oral ingestion delivers concentrations of psilocin equal to intravenous administration of equivalent dose of psilocybin to a subject.

6. The oral psilocin formulation of claim 5 which exhibits decreased patient-to-patient variability as compared to psilocybin treatment.

7. A method for increasing maximum blood concentration (Cmax) of psilocin in a subject compared to equivalent dose of psilocybin administration, said method comprising administering the psilocin formulation of claim 1 to the subject.

8. The method of claim 7 wherein Cmax is at least twice that of an equal amount of psilocin generated by metabolism of psilocybin.

9. The method of claim 7 wherein the subject experiences an anti-anxiolytic effect.

10. The method of claim 7 wherein the subject exhibits no or less hallucinogenic effect as compared to a subject administered an equal amount of psilocin generated by metabolism of psilocybin.

11. The method of claim 7 wherein the psilocin formulation is administered orally to the subject.

12. The method of claim 7 wherein the psilocin formulation is administered daily to the subject.

13. A method for increasing bioavailability of psilocin in a subject as compared to an equal amount of psilocin generated by metabolism of psilocybin, said method comprising administering the psilocin formulation of claim 1 to the subject.

14. The method of claim 13 wherein the subject experiences an anti-anxiolytic effect.

15. The method of claim 13 wherein the anti-anxiolytic effect is sustained.

16. The method of claim 13 wherein the subject exhibits no or less hallucinogenic effect as compared to a subject administered an equal amount of psilocin generated by metabolism of psilocybin.

17. The method of claim 13 wherein the psilocin formulation is administered orally to the subject.

18. The method of claim 13 wherein the psilocin formulation is administered daily to the subject.

19. A method for more rapidly treating a disease or condition in a subject treatable with psilocin or psilocybin as compared to an equivalent amount of psilocybin treatment, said method comprising administering to the subject the psilocin formulation of claim 1.

20. A method for producing a psilocin salt with stability for 12 or more months, said method comprising mixing psilocin with galactaric acid (mucic acid).

* * * * *